United States Patent [19]

Hawrot et al.

[11] Patent Number: 4,948,590

[45] Date of Patent: Aug. 14, 1990

[54] AVIDIN OR STREPTAVIDIN CONJUGATED LIPOSOMES

[75] Inventors: Edward Hawrot, New Haven, Conn.; Michael B. Rosenberg, San Diego, Calif.; Xandra O. Breakefield, Newton, Mass.

[73] Assignee: Yale University, New Haven, Conn.

[21] Appl. No.: 60,140

[22] Filed: Jun. 9, 1987

[51] Int. Cl.[5] .......................... A61K 37/22; C08H 1/00
[52] U.S. Cl. ..................................... 424/450; 530/399; 530/403; 530/404; 530/405; 530/406; 424/455; 436/829
[58] Field of Search ........................ 530/406, 403–405, 530/399; 424/450, 455; 436/829

[56] References Cited

U.S. PATENT DOCUMENTS 4,762,915  8/1988  Kung et al. ...................... 530/405

OTHER PUBLICATIONS

Hilpert et al., "Reconstruction of Na+ Transport from Purified Methylmalonyl-CoA Decarboxylase and Phospholipid Vesicles", Eur. J. Biochem., vol. 138, pp. 579–583, (1984).
Matthay et al., "Specific Enhancement of Drug Delivery to AKR-Lymphoma by Antibody-Targeted Small Unilamellar Vesicles", Cancer Research, vol. 44, pp. 1880–1886, 1984.
Buckel et al., "Purification, Characterization and Reconstruction of Glutaconyl-CoA Decarboxylase, a Biotin-Dependent Sodium Pump from Anaerobic Bacteria", Eur. J. Biochem., vol. 136, pp. 427–434, (1983).
Urdal et al., "Tumor-Associated Ganglio-N-Triosylceramide-Target for Antibody-Dependent, Avidin-Mediated Drug Killing of Tumor Cells", Journal of Biological Chemistry, vol. 255, No. 21, pp. 10509–10516, 1980.
Fraley et al., "Liposome-Medicated Delivery of Deoxyribonucleic Acid to Cells: Engaged Efficiency of Delivery Related to Lipid Composition and Incubation Conditions", Biochemistry, vol. 20, pp. 6978–6987, 1981.
Rosenberg et al., "Receptor Binding Activites of Biotinylated Derivatives of B-Nerve Growth Factor", Journal of Neurochemistry, vol. 46, No. 2, pp. 641–648, 1986.
Mayhew et al., "Therapeutic Application of Liposomes", Liposomes, (M. J. Ostro, ed.), pp. 289–341, Marcel Dekker, Inc., New York, 1983.
"Development of Liposomes as an Efficient Carrier System: New Methodology for Cell Targeting and Intracellular Delivery of Drugs and DNA", Paphadjopoulos, D., et al., pp. 375–391.
G. Gregoriadis, "Use of Monoclonal Antibodies and Liposomes to Improve Drug Delivery. Present Status and Future Implications", Drugs, 24, 261–266, (1982).
E. Mayhew and D. Papahadjoupoulos, "Therapeutic Applications of Liposomes", Liposomes, (M. J. Ostro, ed.), pp. 289–341, Marcell Dekker, New York, (1983).
J. N. Weinstein and L. D. Leserman, "Liposomes as Drug Carriers in Cancer Chemotherapy", Pharmacol. Ther., 24, 207–233, (1984).
V. O. Ivanov, S. N. Preobrazrazhensky, V. P. Tsibulsky, V. R. Babaev, V. S. Repin and V. N. Smirnov, "Liposome Uptake by Cultured Macrophages Mediated by Modified Low-Density Lipoproteins", Biochim. Biophys. Acta, 846, 76–84, (1985).
A. G. Gitman, A. Graessmann and A. Loyter, "Targeting of Loaded Sendai Virus Envelopes by Covalently Attached Insulin Molecules to Virus Receptor-Dep- (List continued on next page.)

Primary Examiner—Margaret Moskowitz
Assistant Examiner—Abdel A. Mohamed
Attorney, Agent, or Firm—Sprung Horn Kramer & Woods

[57] ABSTRACT

A liposome conjugated with a streptavidin compound, wherein carboxyl residues of the streptavidin are coupled to phospholipid amino groups of the liposome. The resultant streptavidin-conjugated liposome can be used to encapsulate drugs and cytotoxic agents for site-specific in vivo or ex corpra targeting.

12 Claims, 8 Drawing Sheets

OTHER PUBLICATIONS leted Cells: Fusion-Mediated Microinjection of Ricin A and Simian Virus 40 DNA", *Proc. Natl. Acad. Sci. U.S.A.*, 82, 7309-7313, (1985).

M. B. Rosenberg, E. Hawrot and X. O. Breakefield, "Receptor Binding Activities of Biotinylated Derivatives of Beta-Nerve Growth Factor", *J. Neurochem.*, 46, 641-648, (1986).

David L. Urdal and Sen-itiroh Hakomori, "Tumor-Associated Ganglio-N-Triosylceramide", *The Journal of Biological Chemistry*, vol. 255, No. 21, 10509-10516, (1980).

M. J. Ostro, "Liposomes", *Scientific American*, Jan., 1987, pp. 103 to 111.

AVIDIN OR STREPTAVIDIN CONJUGATED LIPOSOMES

GOVERNMENT RIGHTS

This invention was made with United States government support under Grants NS 17803, 18281, CA 28852, GM 34536 awarded by the National Institute of Health. The United States government has certain rights in this invention.

BACKGROUND OF THE INVENTION

1. Field of the Invention

The present invention concerns streptavidin or avidin conjugated large unilammelar liposomes.

2. Background Information

The potential use of liposomes as carriers for the cell-specific delivery of macromolecules, the recognition mediated by specific cell surface markers, has attracted much interest in recent years (G. Gregoriadis, "Use of Monoclonal Antibodies and Liposomes to Improve Drug Delivery. Present Status and Future Implications", Drugs, 24, 261-266, (1982); D. Papahadjopoulos, T. Heath, F. Martin, R. Fraley and R. Straubinger, "Development of Liposomes as an Efficient Carrier System: New Methodology for Cell Targeting and Intracellular Delivery of Drugs and DNA", Targeting of Drugs, (G. Gregoriadis, J. Senior and A. Trouet, eds), pp. 375-391. Plenum Press, New York, (1982); E. Mayhew and D. Papahadjopoulos, "Therapeutic Applications of Liposomes", Liposomes, (M. J. Ostro, ed.), pp. 289-341, Marcell Dekker, New York, (1983); J. N. Weinstein and L. D. Leserman, "Liposomes as Drug Carriers in Cancer Chemotherapy", Pharmacol. Ther., 24, 207-233, (1984)).

Such targeted delivery systems should prove advantageous for drug delivery and gene transfer as they would permit directed incorporation of selected macromolecules into the appropriate cell type, while avoiding side effects due to nonspecific interactions with other cell types. Several groups have studied cell-specific delivery of liposomal contents using model in vitro culture systems. The general approach used in most of these studies has involved immunologically based targeting systems, and has relied on the availability of monoclonal antibodies that recognize histocompatibility antigens, or of antisera obtained against cell type-specific surface proteins In contrast, targeting of liposomes via ligand-receptor interactions has received less attention, although low density lipoproteins (V. O. Ivanov, S. N. Preobrazhensky, V. P. Tsibulsky, V. R. Babaev, V. S. Repin and V. N. Smirnov, "Liposome Uptake by Cultured Macrophages Mediated by Modified Low-Density Lipoproteins", Biochem. Biophys. Acta, 846, 76-84, (1985)) and insulin (A. G. Gitman, A. Graessmann and A. Loyter, "Targeting of Loaded Sendai Virus Envelopes by Covalently Attached Insulin Molecules to Virus Receptor-Depleted Cells: Fusion-Mediated Microinjection of Ricin A and Simian Virus 40 DNA", Proc. Natl. Acad. Sci. U. S. A., 82, 7309-7313, (1985)) have been utilized in this manner.

Applicants have previously demonstrated that the polypeptide hormone beta-nerve growth factor (NGF) can be chemically modified by biotinylation via its carboxyl groups (C-bio-NGF) without loss of binding activity for specific NGF receptors on rat PC12 pheochromocytoma cells (M. B. Rosenberg, E. Hawrot and X. O. Breakefield, "Receptor Binding Activities of Biotinylated Derivatives of Beta-Nerve Growth Factor", J. Neurochem, 46, 641-648, (1986)). In addition, C-bio-NGF is fully active in promoting neurite outgrowth from PC12 cells. Further, C-bio-NGF was shown to mediate the specific binding of the biotin-binding protein, streptavidin, to these cells, but not to a variant line of PC12 cells lacking NGF receptors.

Heretofore procedures for coupling proteins, such as streptavidin, to the outer surface of liposomes have generally used disulfide bond linkages. Such linkages may not be very stable in vivo. David L. Urdal and Sen-itiroh Hakomori, "Tumor-associated Ganglio-N-triosylceramide", The Journal of Biological Chemistry, Vol. 255, No. 21, 10509-10516 (1980) describe reductive amination to link avidin to liposomes.

Liposomes and their potential use for delivering medicines is described by M. J. Ostro, "Liposomes", Scientific American, January, 1987, pp. 103 to 111.

SUMMARY OF THE INVENTION

It is one aim of the present invention to take advantage of the naturally restricted expression of hormone receptors on specific cell types to effect directed delivery of liposomes.

It is another aim of the present invention to achieve cell-specific targeting using streptavidin-conjugated liposomes.

These aims and other aims and advantages are provided by the present invention wherein a protein capable of binding biotin, e.g., streptavidin or avidin, is conjugated to phospholipid amino groups on a liposome prepared by, e.g., reverse-phase evaporation. More particularly, liposomes according to the invention are prepared by carbodiimide-mediated coupling of carboxyl residues on streptavidin to amino groups residing on phosphatidylethanolamine molecules residing in preformed large unilammelar liposomes.

The avidin- or streptavidin-conjugated liposomes of the present invention can be utilized as a vehicle for site-specific targeting of a wide variety of encapsulated drugs or other macromolecules Accordingly, the present invention concerns a method for site-specific targeting of drugs or cytotoxic agents in a host, e.g., a human or animal, comprising (a) encapsulating the drug, e.g., an antibiotic, e.g., streptomycin, an antigen (liposomal vaccine), or cytotoxic agent within an avidin- or streptavidin-conjugated liposome as described hereinabove, (b) attaching biotin or a biotin-containing compound to a ligand or antibody for said site, (c) introducing the product of step (b) into the host and (d) introducing the product of step (a) into the host.

Also the product of step (b) could be combined with the product of step (a) and this new product could be introduced into the host.

In certain cases, for example, gene delivery to white blood cell precursors, the liposomes of the present invention would be added to tissue samples ex corpora for site specific targeting, then the tissue would be reintroduced into the host.

BRIEF DESCRIPTION OF THE DRAWINGS

FIG. 3 constitutes two sets of bar graphs showing the effects of temperature on liposome targeting.

FIG. 4 depicts the initial binding of FITC-D-containing liposomes to cells. FIG. 4A is a photograph of a fluorescence micrograph and FIG. 4B is a photograph of the corresponding phase-contrast field. FIG. 4C is a photograph of a fluorescence micrograph and FIG. 4D is a photograph of the corresponding phase-contrast field FIG. 4E and FIG. 4F concern HS294 cells with targeted binding.

FIG. 5 depicts FITC-D distribution in attached cells.

FIG. 6 depicts the trypsin removal of surface-bound fluorescence HS294 cells labeled with liposomes containing FITC-D. FIG. 6A and FIG. 6C are photographs of fluorescence micrographs. FIG. 6B and FIG. 6D are photographs of the corresponding phase-contrast field Bar equals 20 μm.

FIG. 7 depicts the uptake of CF by HS204 cells. FIG. 7A and FIG. 7C are photographs of fluorescence micrographs. FIG. 7B and FIG. 7D are photographs of the corresponding phase-contrast fields Bar equals 20 μm.

DETAILED DESCRIPTION OF THE INVENTION

Figure 1:
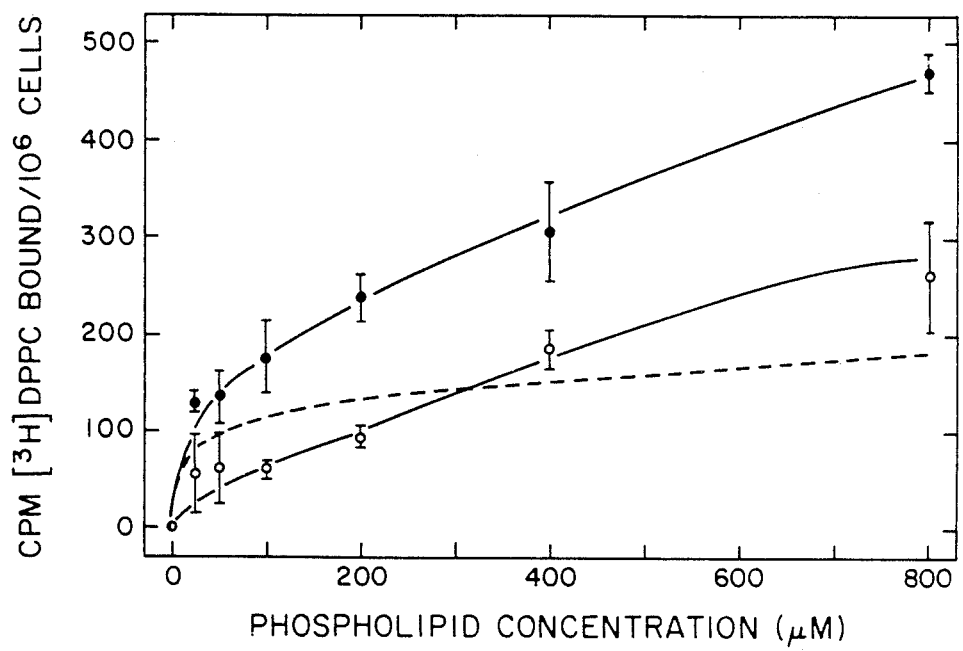
FIG. 1 is a concentration curve for radiolabeled liposome binding to PC12 cells. Specific binding of targeted liposomes (---) was determined by subtracting nonspecific binding (Hb-liposomes, O) from total binding (SA-liposomes, ●).

Liposomes consist of spheres of lipid bilayers (two-molecules thick) that enclose an aqueous medium.

Liposomes can generally be formed by sonicating a lipid in a aqueous medium, by resuspension of dried lipid layers in a buffer or by dialysis of lipids dissolved in an organic solvent against a buffer of choice.

Phospholipids form closed, fluid-filled spheres when they are mixed with water in part because the molecules are amphipathic: they have a hydrophobic (water-insoluble) tail and a hydrophilic (water-soluble), or "polar," head. Two fatty acid chains, each containing from 10 to 24 carbon atoms, make up the hydrophobic tail of most naturally occurring phospholipid molecules. Phosphoric acid bound to any of several water-soluble molecules composes the hydrophilic head. When a high enough concentration of phospholipids is mixed with water, the hydrophobic tails spontaneously herd together to exclude water, whereas the hydrophilic heads bind to water.

The result is a bilayer in which the fatty acid tails point into the membrane's interior and the polar head groups point outward. The polar groups at one surface of the membrane point toward the liposome's interior and those at the other surface point toward the external environment. It is this remarkable reactivity of phospholipids to water that enables workers to load medications into liposomes. As a liposome forms, any water-soluble molecules that have been added to the water are incorporated into the aqueous spaces in the interior of the spheres, whereas any lipid-soluble molecules added to the solvent during vesicle formation are incorporated into the lipid bilayer.

Liposomes employed for drug delivery typically range in diameter from 250 angstrom units to several micrometers (the diameter of a red blood cell is roughly 10 micrometers) and are usually suspended in a solution. They have two standard forms: "onion-skinned" multilamellar vesicles (MLV'S), made up of several lipid bilayers separated by fluid, and unilamellar vesicles, consisting of a single bilayer surrounding an entirely fluid core. The unilamellar vesicles are typically characterized as being small (SUV'S) or large (LUV'S). The unilamellar vesicles are preferred in the present application.

Under appropriate circumstances liposomes can adsorb to almost any cell type. Once they have adsorbed the spheres, liposomes may be endocytosed, or swallowed up, by some cells. Adsorbed liposomes can also exchange lipids with cell membranes and may at times be able to fuse with cells. When fusion takes place, the liposomal membrane is integrated into the cell membrane and the aqueous contents of the liposome merge with the fluid in the cell.

The ability of liposomes to adsorb to virtually any type of cell and to then release their contents slowly makes them excellent candidates for time-release drug-delivery systems. Multilamellar liposomes are particularly effective in this regard because the fluid in each successive layer is released only after the lipid membrane around it is degraded by the body or otherwise punctured. How quickly a drug is released from an adsorbed liposome depends on many factors, including the composition of the liposome, the type of drug encapsulated and the nature of the cell. Once it is released, a drug that normally crosses the membrane of a cell will enter the cell; other drugs will not enter.

Endocytosis of liposomes occurs in a limited class of cells; those that are phagocytic, or able to ingest foreign particles. When phagocytic cells take up liposomes, the cells move the spheres into subcellular organelles known as lysosomes, where the liposomal membranes are thought to be degraded From the lysosome the liposomal lipid components probably migrate outward to become part of the cell's membranes and other liposomal components that resist lysosomal degradation (such as certain medications) may enter the cytoplasm.

Lipid exchange involves the transfer of individual lipid molecules from the liposome into the plasma membrane (and vice versa); the aqueous contents of the liposome do not enter the cell. For lipid exchange to take place the liposomal lipid must have a particular chemistry in relation to the target cell. Once a liposomal lipid joins the cell membrane it can either remain in the membrane for a long time or be redistributed to a variety of intracellular membranes. If a drug was somehow bound to such an exchangeable lipid, it could potentially enter the cell during lipid exchange.

The liposome of the present invention is conjugated with a protein that contains carboxyl residues and is capable of binding biotin. Such protein can be, for example, avidin (glycosylated and obtained from eucaryotic sources), streptavidin (non-glycosylated and obtained from procaryotic sources) and anti-biotin antibodies.

Biotin is a low molecular weight, optically active organic acid, and the active form is the d isomer. The vitamin has the following structural formula:

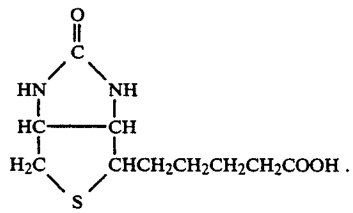

Three forms of biotin, apart from free biotin itself, have been found in natural materials. These derivatives are biocytin (ε-biotinyl-L-lysine) and the D and L sulfoxides of biotin.

Unmodified avidin purified from egg white displays a significant amount of nonspecific binding to solid-phase surfaces This problem can be overcome by the use of succinylated avidin or other avidin preparations with decreased rates of nonspecific binding. Avidin from *Streptomyces* spp. can also be utilized in place of avidin from egg white. If these avidin preparations are utilized, efficient avidin-biotin systems can be formulated with minimal degrees of nonspecific interactions.

Besides biotin, the following forms of biotin can be used in the present invention: biocytin, D-sulfoxide of biotin, L-sulfoxide of biotin, biotin sulfane and desthiobiotin.

Non-limiting examples of drugs and other macromolecules that may be encapsulated in the avidin- or streptavidin-conjugated liposomes according to the present invention including the following: methotrexate and its congeners, fluorouracil, arabinosyl adenine (Ara-A), cytosine arabinoside (Ara-C), actinomycin-D, mitomycin-C, adriamycin, mercaptopolycytosine. These drugs include inhibitors of key metabolic enzymes as well as agents that cross-link DNA and would thus be most effective against rapidly dividing cells such as targeted cancer cells.

Various protein toxins that could also be encapsulated according to the present invention include, for example, ricin A or diptheria toxin. These agents could serve to kill targeted cells Such agents could be used to kill tumor-associated capillary endothelial cells thus disrupting the essential blood supply of solid tumors.

Liposomes of the present invention could be used to encapsulate enzymes for enzyme replacement therapy or possibly antibodies for insertion into the cell interior. One embodiment would be to encapsulate antibodies made against AIDS virus proteins and to target these antibodies to infected T lymphocytes. The antibodies could thus disrupt the assembly of the virion and could prevent cell death. A notable advantage to this strategy would be the fact that antibodies could be used even though they may not directly interfere with cell infection per se. This latter step is the one most often strived for with standard antibody strategies but is often difficult to achieve. Other antiviral agents such as cyclovir, in the case of herpes virus, could be targeted to infected cells and may thus enhance the action of the antiviral agents. For example, encapsulated cyclovir could be targeted to herpes infected peripheral sensory neurons by way of the NGF-receptor since these neurons have NGF-receptors on their cell surface. The drug could then act on the quiescent virus within the neuronal cell bodies and thus effect a permanent or long-lasting cure. A similar strategy would apply to any potential anti-AIDS virus drugs. By effecting the injection of the drug directly into the infected T cells, significant enhancement of drug efficacy could be obtained.

DNA could be encapsulated according to the present invention to achieve gene replacement therapy for various genetic diseases or to introduce a gene for methotrexate resistance into blood cell precursors so that higher doses of methotrexate could be administered without serious side effects on the hematopoietic system. Retrovirus vectors containing the desired gene could be encapsulated for cell-specific delivery. The retrovirus vector would facilitate stable incorporation of genetic material into the host chromosome. Antisense RNA complementary to particular mRNA classes could be encapsulated also at a means of disrupting ongoing metabolism or possibly the production of viral DNAs or RNAs.

Antiparasitics could also be encapsulated according to the present invention and targeted to infected cells, e.g., red blood cells.

In summary, it is noted that with a specific surface antigen associated with proliferating endothelial cells, liposomes according to the invention containing cytotoxic agents therein could be used to specifically disrupt the vasculature within tumors, thus leading to tumor cell death due to insufficient oxygen delivery.

The invention is now described with reference to the following non-limiting examples.

EXAMPLES

Example 1: Preparation of Biotinylated NGF Derivatives

NGF was isolated from the submaxillary glands of adult male mice (W. C. Mobley, A. Schenker and E. M. Shooter, "Characterization and Isolation of Proteolytically Modified Nerve Growth Factor", *Biochemistry,* 15, 5543–5552, (1976)) and was biotinylated via its carboxyl groups (C-bio-NGF) as described by Rosenberg et al (1986), supra.

A biotinylated NGF derivative with an extended spacer arm, biocytin-NGF, was also synthesized. Biocytin (N-ε-biotinyl-L-lysine, Sigma) was dissolved in 5 mg/ml in absolute methanol containing 0.1M HCl and incubated 48 hours at 37° C. Conversion of biocytin to the methyl ester was essentially quantitative, as determined by TLC on silica gel plates (Linear-K, Whatman) developed in 80 ml methanol and 10 ml $H_2O$. Biocytin was detected on the plates colorimetrically, by spraying with an ethanolic solution of p-dimethylamino- cinnamaldehyde (N. M. Green, "Spectrophotometric Determination of Avidin and Biotin", *Methods Enzymol.,* 18A, 418–424, (1970)).

The biocytin methyl ester was dried under a stream of nitrogen and redissolved at 5 mg/ml in 10 mM pyridine HCl, pH 4.8, containing 100 mM NaCl (pyridine buffer).

NGF (400 μg, 15 nmol) in 200 μl Dulbecco's phosphate-buffered saline (PBS), plus a trace amount of $^{125}$I-NGF (Rosenberg et al, 1986, supra, was mixed with 11.2 mg (7.5 μmol) biocytin methyl ester and 12 mg (15 μmol) of the coupling reagent 1-ethyl-3-(3-dimethylaminopropyl)carbodiimide (EDAC, Sigma). The solution was incubated 16 hours at 23° C. Bovine serum albumin (BSA, fraction V, Sigma) was added to a final concentration of 2 mg/ml, and the solution was concentrated and transferred to PBS by ultrafiltration (Amicon YM-5 membrane). The final NGF concentration was determined radiometrically and the biotin content was determined by the method of D. B. McCormick and J. A. Roth, "Colorimetric Determination of Biotin and Analogs", *Methods Enzymol*, 18A, 383–385, (1970), as described by Rosenberg et al (1986), supra. Each NGF monomer contained an average of three biotin moieties. Essentially no native NGF remained following the reaction, as determined by sodium dodecyl sulfate and nonequilibrium pH gradient polyacrylamide gel electrophoresis, as described by Rosenberg et al, (1986), supra.

Example 2: Preparation of Liposomes

Lipids were purchased from Sigma and stored in 9:1 chloroform/methanol under nitrogen at −20° C. Phospholipid concentrations were determined by the colorimetric method of W. R. Morrison, "A Fast, Simple and Reliable Method for the Microdetermination of Phosphorus in Biological Materials", *Anal. Biochem.*, 7, 218–224, (1964), which uses ammonium molybdate to detect inorganic phosphate in acid-hydrolyzed samples. Liposomes were formed by the reverse-phase evaporation method (F. Szoka, Jr. and D. Papahadjopoulos, "Procedure for Preparation of Liposomes with Large Internal Aqueous Space and High Capture by Reverse-Phase Evaporation", *Proc. Natl. Acad. Sci., U. S. A.*, 75, 4194–4198, (1978)).

Ten micromoles of cholesterol, 8 μmol of egg phosphatidylcholine (PC), 1.95 μmol of dipalmitoyl phosphatidylethanolamine (DPPE), and 50 nmol dicetyl phosphate were dried under a stream of nitrogen in a 13×100 mm screw cap Kimax test tube (Kimble). In some experiments, 20 μCi of $^{3}$H-labeled dipalmitoyl PC (2-palmitoyl-9,10-$^{3}$H(N)-PC, sp act 30–60 Ci/mmol, New England Nuclear) was also included. HPLC-grade ethyl ether without preservatives (Mallinckrodt) was shaken 5 minutes, under nitrogen, with an equal volume of 5% sodium sulfite to eliminate peroxides. The dried lipids were dissolved in 1 ml of the treated ether, and then 333 μl of 10 mM 4-(2-hydroxyethyl)-1-piperazineethane-sulfonic acid (HEPES), pH 7.4, containing 100 mM NaCl (HEPES buffered saline, HBS) were added. In some experiments, the hemoglobin-conjugated liposomes (HBS) also contained fluorescein isothiocyanate-dextran (FITC-D, average molecular weight 70,000 daltons, Sigma), at a fluorescein concentration of 10 mM. The tube was flushed with nitrogen, sealed with a "TEFLON"-lined cap, and sonicated in an 80 Watt bath-type sonicator (Heat Systems-Ultrasonics) for 1–2 minutes at 23° C. until a uniform emulsion formed. The ether was removed under reduced pressure at 23° C. on a rotary evaporator. After a viscous gel formed, the tube was vortex-mixed briefly, and evaporation was continued. When a liposome suspension formed, 667 μl of HBS were added. The tube was again vortex-mixed, to disrupt aggregates of vesicles, and evaporation was continued for 30 minutes to remove as much residual ether as possible. Liposomes were separated from unincorporated material by flotation on Ficoll gradients (R. Fraley, S. Subramani, P. Berg, and D. Papahadjopoulos, "Introduction of Liposome-Encapsulated SV40 DNA Into Cells", *J. Biol. Chem.*, 255, 10431–10435, (1980)). Liposome suspensions were mixed with equal volumes of 40% Ficoll 400 (Pharmacia) in HBS and transferred to 0.5×2 inch cellulose nitrate or polyallomer ultracentrifuge tubes. They were overlaid with 10% Ficoll in pyridine buffer to a total volume of 4.5 ml, and then topped with 1 ml pyridine buffer. The tubes were centrifuged 30 minutes at 100,000 g (Beckman SW 50 or SW 55 rotor), and the liposomes, which banded at the interface between the pyridine buffer and 10% Ficoll, were collected in 1 ml.

Liposomes were also prepared containing carboxyfluorescein (CF, Kodak) by the above procedure, modified as follows to prevent CF efflux from the vesicles at low pH (R. M. Straubinger, K. Hong, D. S. Friend and D. Papahadjopoulos, "Endocytosis of Liposomes and Intracellular Fate of Encapsulated Molecules: Encounter with a Low pH Compartment After Internalization in Coated Vesicles", *Cell*, 32, 1069–1079, (1983)). CF was purified as described by J. N. Weinstein, E. Ralston, L. D. Leserman, R. D. Klausner, P. Dragsten, P. Henkart and R. Blumenthal, "Self-quenching of Carboxyfluorescein: Uses in Studying Liposome Stability and Liposome-cell Interaction", *Liposome Technology*, (G. Gregoriadis, ed), pp. 183–204, (1984), CRC Press, Boca Raton, Fla., and used at 100 mM in PBS in place of HBS for preparing liposomes. After the liposome suspension formed, 667 μl of PBS were added instead of HBS. The liposomes were centrifuged through Ficoll gradients as described, substituting 10 mM Na phosphate, pH 6.5, containing 0.15 M NaCl, for the pyridine buffer.

Example 3: Conjugation of Streptavidin to Liposomes

Liposomes in 0.5 ml pyridine or phosphate buffer were mixed with 1 mg streptavidin (BRL) in 0.5 ml of the same buffer, and 100 mg EDAC were added. In some experiments, a trace amount of $^{125}$I-streptavidin (3–10 cpm/pg, Rosenberg et al, 1986, supra) was incubated to monitor the extent of conjugation. Control liposomes were prepared with hemoglobin instead of streptavidin. The mixtures were incubated for 16 hours under nitrogen at 23° C., mixing end-over-end, and liposomes were separated from free protein on Ficoll gradients as described above, except that HBS was substituted for pyridine buffer in the two top layers (PBS was used for carboxyfluorescein (CF)-containing liposomes). The liposomes were collected in a minimal volume and adjusted to an approximate phospholipid concentration of 5 μmol/ml. The suspensions were stored under nitrogen at 4° C. and were stable for up to 6 weeks.

Example 4: Cell Culture

Rat pheochromocytoma PC12 cells were grown as monolayer cultures in Dulbecco's modified Eagle's medium (DMEM, Gibco) containing 10% fetal bovine serum (HyClone), 5% heat-inactivated donor horse serum (K. C. Biologicals), and 50 μg/ml gentamicin sulfate (GIBCO). Human melanoma HS294 cells were grown as monolayer cultures in DMEM containing 10% fetal bovine serum and 50 μg/ml gentamicin sulfate (D10 medium).

Example 5: PC12 Bioassay for NGF

PC12 cells were seeded at $5 \times 10^3$ cells per well in poly-D-lysine-treated 16 mm tissue culture wells (NUNC) and grown in 1 ml of culture medium supplemented with up to 3.2 ng/ml NGF, C-bio-NGF, or biocytin-NGF. After 5, 7, 9 and 11 days, the cells were examined microscopically and random fields were scored for the percentage of cells bearing neurites at least two cell body diameters in length. Approximately 100 cells were counted for each NGF concentration on each day.

Example 6: Liposome-cell Incubations

PC12 cells were harvested by gentle trituration in PBS; HS294 cells were harvested by trituration in PBS containing 1 mM EDTA. Cells were centrifuged at 700 g for 3 minutes and resuspended at $10^6$–$10^7$/ml in DMEM containing 10 mM HEPES, pH 7.4, 1 mg/ml BSA, and 0.1 mg/ml cytochrome c(HB-DMEM). Both proteins reduced nonspecific binding of NGF to cells. This buffer was used for all subsequent incubations and washes. The cells were incubated with 200–1,000 ng/ml NGF, C-bio-NGF, or biocytin NGF for 2 hours at 4, 23 or 37° C., in 12×75 mm conical polypropylene test tubes (American Scientific Products), with end-over-end mixing. They were then centrifuged as described above, washed twice and resuspended at $3$–$5 \times 10^6$/ml. Aliquots of 480 μl were incubated with 20 μl of streptavidin- or hemoglobin-conjugated liposomes for 45 minutes at 4° C., mixing end-over-end.

When radiolabeled liposomes were used, cells were separated from unbound liposomes in 400 μl polypropylene microcentrifuge tubes containing 100 μl 0.15M sucrose in PBS layered over 50 μl of 0.3M sucrose in PBS. Three 150-μl aliquots of cells from each incubation tube were layered onto three sucrose tubes, which were then centrifuged for 3 minutes in a microcentrifuge at 13,000 g. The supernatants were removed by aspiration, the bottom 5 mm of the tubes were cut off, and the cell pellets were dissolved in 400 μl of an aqueous solution of 1% sodium dodecyl sulfate for 30 minutes at 23° C. After the addition of 3.5 ml of Liquiscint (National Diagnostics), cell-associated radioactivity was assayed in a liquid scintillation counter (Beckman).

When liposomes containing fluorescein isothiocyanate-conjugated dextran (FITC-D) or CF were used, cells were separated from unbound vesicles as described above, except that 150 μl of 8.5% Ficoll in PBS was substituted for sucrose, and the centrifugation time was reduced to 12 s. The cell pellets were resuspended on 150 μl of HB-DMEM and viewed with a Zeiss inverted microscope equipped with epifluorescence optics (excitation, 450–490 nm; emission, 510–515 nm). In several experiments, the resuspended cells were then added to DMEM with 10% fetal bovine serum (D10) medium at a concentration of $1$–$2 \times 10^5$ cells/ml and 0.75-ml aliquots were plated onto 4-well Lab Tek chamber slides (Miles); poly-D-lysine-coated plastic slides were used for PC12 cells and untreated glass slides were used for HS294 cells. The cultures were incubated at 37° C. for up to 20 hours in a $CO_2$ culture incubator and viewed periodically. Cell viability after these treatments was greater than 70%, as determined by trypan blue exclusion.

Example 7: Acridine Orange Staining of Lysosomes

HS294 cells, cultured overnight on Lab Tek slides as described above, were incubated 15 minutes at 37° C. with DMEM with 10% fetal bovine serum D10 containing 5 μg/ml acridine orange (Sigma) (M. C. Kielian and Z. A. Cohn, "Phagosome-lysosome Fusion: Characterization of Cellular Membrane Fusion in Mouse Macrophages", *J. Cell Biol.*, 85, 754–765, (1980)). The cells were washed once and incubated 10 minutes at 37° C. with D10 alone. The medium was replaced with PBS. The cells were viewed, as described above, using fluorescein excitation optics and rhodamine emission optics.

Example 8: Photography

Photomicrographs of cells in suspension or attached to Lab Tek slides were taken using "KODAK"Tri-X Pan film, ASA 400. Photographs of fluorescein fluorescence had an exposure time of 2 minutes when glass slides were used and 1 minute when plastic slides were used (because of the higher level of autofluorescence). Acridine orange fluorescence and phase-contrast micrographs were taken with shutter speeds controlled by the automatic setting of the camera (Contax) on the photomicroscope.

RESULTS

Liposome Preparation

The reverse-phase evaporation method of liposome preparation (Szoka and Papahadjopoulos, 1978, supra) was chosen because it produces predominantly large unilamellar vesicles, with a high entrapment efficiency. Approximately 25% of added $^3$H-labeled mannitol was encapsulated. Such vesicles have been shown to entrap efficiently large macromolecules, such as DNA (F. Fraley, S. Subramani, P. Berg and D. Papahadjopoulos, "Introduction of Liposome-Encapsulated SV40 DNA into Cells", *J. Biol. Chem.*, 255, 10431–10435, (1984)) or even retroviruses (D. V. Faller and D. Baltimore, "Liposome Encapsulation of Retrovirus Allows Efficient Superinfection of Resistant Cell Lines", *J. Virol.*, 49, 269–272, (1984)). Fifty mol% cholesterol was included to minimize leakage from the vesicles, (R. Fraley, R. Straubinger, G. Rule, L. Springer and D. Papahadjopoulos, "Liposome-mediated Delivery of DNA to Cells: Enhanced Efficiency of Delivery by Changes in Lipid Composition and Incubation Conditions", *Biochemistry*, 20, 6978–6987, (1981), 40 mol% PC was included to minimize nonspecific binding of liposomes to cells (Fraley et al, 1981, supra) and 9.75 mol% DPPE was included to provide amino groups for the coupling of proteins, i.e., streptavidin and hemoglobin. In addition, 0.25 mol% dicetyl phosphate was included to impart a slight negative charge to the liposomes, which helped to reduce liposome aggregation, without increasing the nonspecific binding to cells (data not shown).

Because each streptavidin tetramer contains a large excess of, carboxyl groups over amino groups (88 and 20, respectively) (N. M. Green, "Avidin", *Adv. Protein Chem.*, 29, 85–133, (1975)), whereas the liposomes contain only amino groups, protein carboxyl groups were chosen to link to liposome amino groups, using the water-soluble carbodiimide EDAC, which we had previously employed to conjugate the amino groups of biotin hydrazide to the carboxyl groups of NGF (Rosenberg et al, 1986, supra). Various concentrations of EDAC were tested; a level of 100 mg/ml resulted in maximal binding of streptavidin to liposomes, as determined by adding trace amounts of $^{125}$I-streptavidin to the reaction mixture (data not shown). Up to 60% of the streptavidin was bound to liposomes, which corresponds to about 2,000 molecules per vesicle, based on the calculations of Szoka and Papahadjopoulos (1978), supra, assuming an average liposome diameter of 0.4 μm. To determine whether EDAC cross-linked liposomes via streptavidin bridges, particle size distributions in liposome preparations made with varying amounts of EDAC were compared to non-conjugated liposomes using a Coulter counter with a particle size display attachment. At EDAC concentrations of up to 100 mg/ml, cross-linking of liposomes was negligible. At an EDAC concentration of 400 mg/ml, however, the vesicles were substantially cross-linked, as there was a marked increase in particle size (data not shown). At EDAC concentration, the level of $^{125}$I-streptavidin conjugated to liposomes was also reduced (date not shown). For comparative purposes, N-hydroxysuccinimidyl 3-(2-pyridyldithio)-propionate, a reagent widely used for conjugating proteins to liposomes via amino group cross-linking (e.g., L. D. Leserman, J. Barbet, F. Kourilsky and J. N. Weinstein, "Targeting to Cells of Fluorescent Liposomes Covalently Coupled with Monoclonal Antibody or Protein", *A. Nature*, 288, 602-604, (1980)), was also tested. This reagent proved to be less efficient than EDAC and yielded more variable results when used for cross-linking streptavidin to liposomes.

For successful conjugations, it was necessary to prepare liposomes using ethyl ether that did not contain butylated hydroxytoluene or similar antioxidants as preservatives. Such compounds have active hydrogen moieties that can substitute for carboxyl groups to react with carbodiimides, (G. E. Means and R. E. Feeney, *Chemical Modification of Proteins*, pp. 144–148, Holden-Day, San Francisco, (1971)). Their presence, therefore, greatly reduced or entirely eliminated the crosslinking of streptavidin to liposomes.

Biocytin-NGF

Previously, it was demonstrated that C-bio-NGF could mediate the specific binding of $^{125}$I-streptavidin to PC12 cells (Rosenberg et al, 1986, supra). It was believed that a derivative of C-bio-NGF with a spacer arm between the protein and biotin moieties might be advantageous for the targeting of liposomes, as the spacer could reduce steric hindrance between the large liposomes and cells. Therefore, the methyl ester of biocytin was used in place of biotin hydrazide to modify NGF, thereby providing an additional five-atom spacer. Biocytin-NGF was indistinguishable from native NGF or C-bio-NGF in its capacity to compete with $^{125}$I-NGF for binding to NGF receptors on PC12 cells and was as effective as native NGF in inducing neurite outgrowth from PC12 cells (data not shown).

Binding of Radiolabeled Liposomes to PC12 Cells

PC12 cells were incubated in suspension at 4° C. with 200 ng/ml C-bio-NGF for 2 hours, washed, and incubated at 4° C. with various concentrations of $^3$H-labeled streptavidin-conjugated liposomes (SA-liposomes) or hemoglobin-conjugated liposomes (Hb-liposomes) for 45 minutes at 4° C. C-bio-NGF mediated the increased binding of SA-liposomes to cells at all concentrations tested, as compared to Hb-liposomes (FIG. 1). Because specific targeted binding reached a maximum level when liposomes were used at a concentration of 200 μM phospholipid, this concentration was used for subsequent experiments. The binding of liposomes to cells was rapid, reaching a maximum level by 15 minutes, which was maintained for at least 60 minutes (data not shown).

Figure 2:
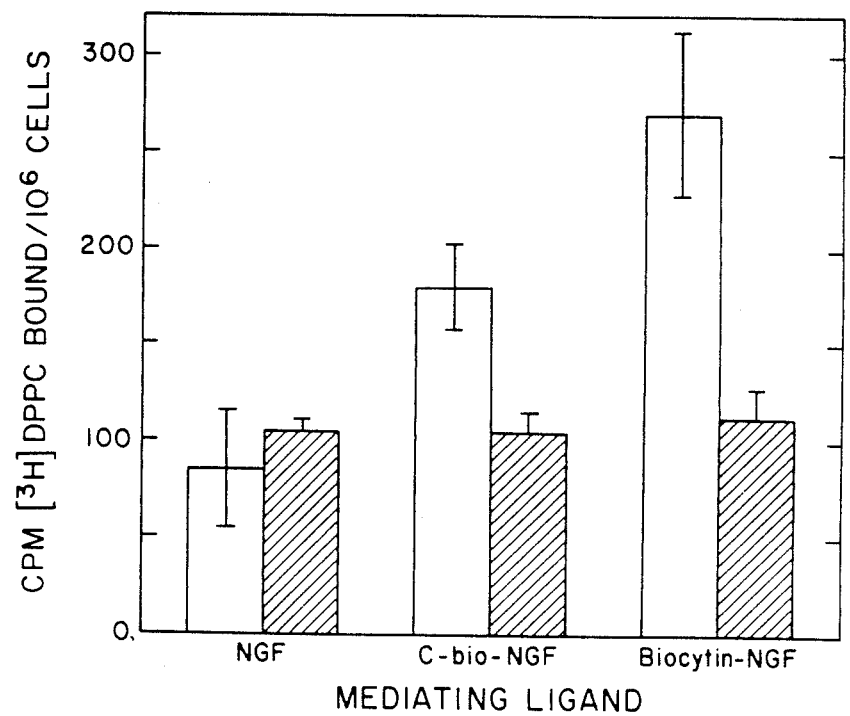
FIG. 2 is a series of bar graphs for comparing NGF, C-bio-NGF and biocytin-NGF in mediating liposome targeting.

FIG. 2 is a comparison of NGF, C-bio-NGF, and biocytin-NGF in mediating liposome targeting. PC12 cells were incubated with 200 ng/ml NGF, C-bio-NGF, or biocytin-NGF for 2 hours at 4° C., washed and incubated with SA-liposomes (open columns or Hb-liposomes (shaded columns) at a concentration of 200 μM phospholipid for 45 minutes at 4° C.

Targeted binding of SA-liposomes was mediated by both C-bio-NGF and biocytin-NGF, but not by unmodified NGF and none of these reagents mediated the binding of Hb-liposomes (FIG. 2). The level of nonspecific binding of SA-liposomes to cells pretreated with unmodified NGF was the same as that of Hb-liposomes (FIG. 2), further demonstrating the specificity of targeted liposome interaction with the cells. The ratio of specific to nonspecific binding mediated by biocytin-NGF was significantly greater than that mediated by C-bio-NGF (2.8 and 1.9, respectively; $p<0.0001$).

Figure 3A:
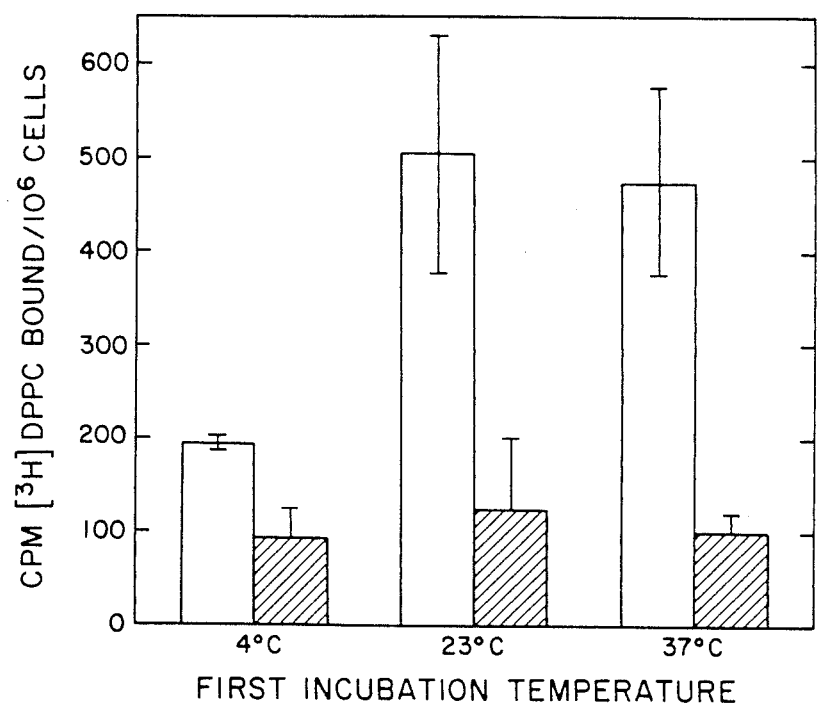
FIG. 3A concerns PC12 cells incubated with C-bio-NGF.
Figure 3B:
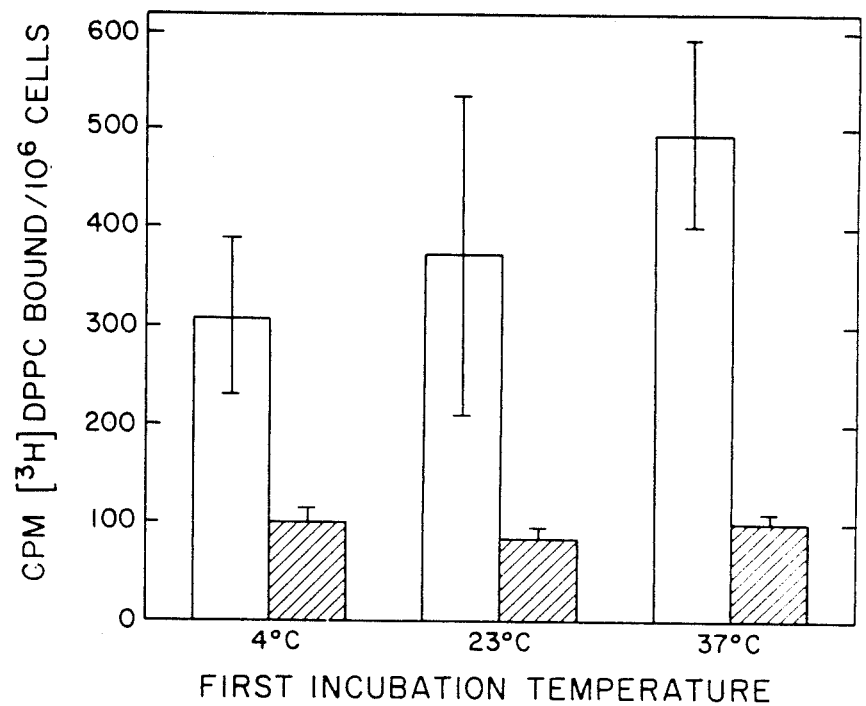
FIG. 3B concerns PC12 cells incubated with biocytin-NGF.

FIG. 3 shows the effects of temperature on liposome targeting. PC12 cells were incubated with 200 ng/ml C-bio-NGF (A) or biocytin-NGF (B) for 2 hours at 4°, 23°, or 37° C., held on ice for 5 minutes, washed, and incubated with SA-liposomes (open columns) or Hb-liposomes (shaded columns) at a concentration of 200 μM phospholipid for 45 minutes at 4° C.

Raising the temperature of the NGF-cell incubation from 4° to 23° and 37° C. resulted in a significant increase in the subsequent specific binding of liposomes (FIG. 3), with targeted to nontargeted ratios of 4.1 and 4.8 for C-bio-NGF and 4.4 and 5.0 for biocytin-NGF ($p<0.05$ for biocytin-NGF at 23° C., $p<0.0001$ for all other conditions). The differences between C-bio-NGF and biocytin-NGF were not significant at these temperatures ($p>0.35$), nor were the differences between 23° and 37° C. for either derivative ($p>0.1$ for bio-NGF, $p>0.25$ for biocytin-NGF). Using biocytin-NGF at 37° C. yielded an average of approximately 570 liposomes specifically bound per cell, based on the calculations of Szoka and Papahadjopoulos (1978), supra.

Binding of Fluorescent Liposomes to PC12 Cells and Melanomas

FIG. 4 depicts initial binding of FITC-D-containing liposomes to cells. PC12 or HS294 cells were incubated with SA-liposomes containing FITC-D following prior incubation with 1 μg/ml biocytin-NGF (targeted binding) or unmodified NGF (control). After the cells were separated from free liposomes by centrifugation through 8.5% Ficoll, they were resuspended in HB-DMEM and photographed on glass slides under glass coverslips.

Figure 4D:
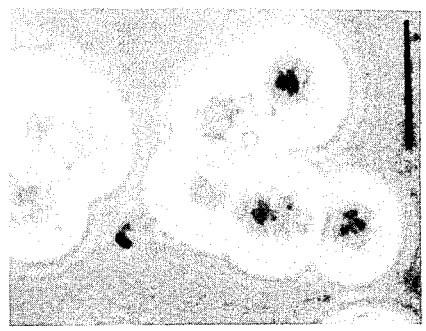
FIG. 4C and FIG. 4D concern PC12 cells with control binding.
Figure 4C:
Figure 4B:
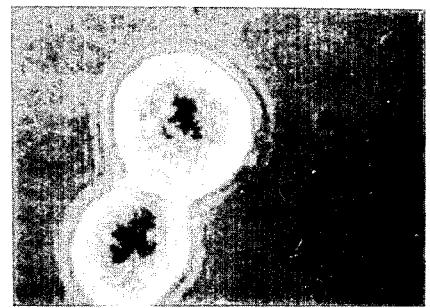
FIG. 4A and FIG. 4B concern PC12 cells with targeted binding.
Figure 4A:
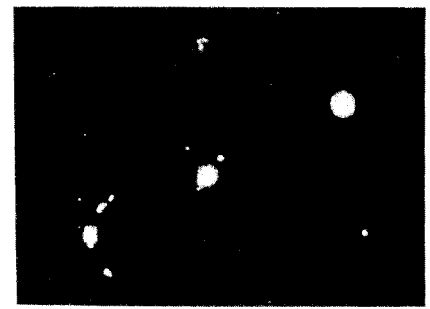
Figure 4F:
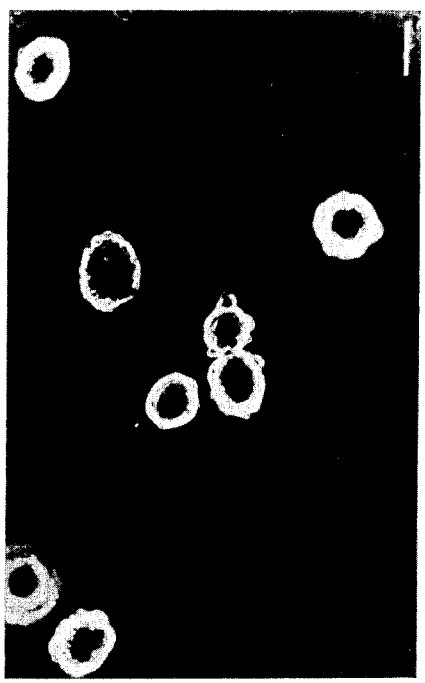
FIG. 4E is a photograph of a fluorescence micrograph and FIG. 4F is a photograph of a corresponding phase-contrast field FIG. 4G and FIG. 4H concern HS294 cells with control binding.
Figure 4H:
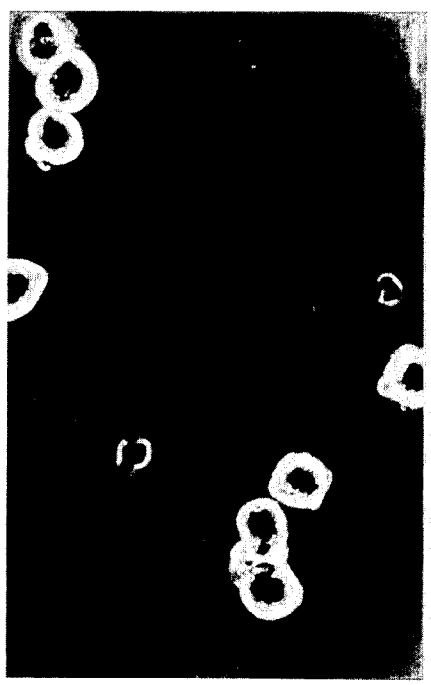
FIG. 4G is a photograph of a fluorescence micrograph and FIG. 4H is a photograph of a corresponding phase-contrast field. Bar equals 20 μm.
Figure 4E:
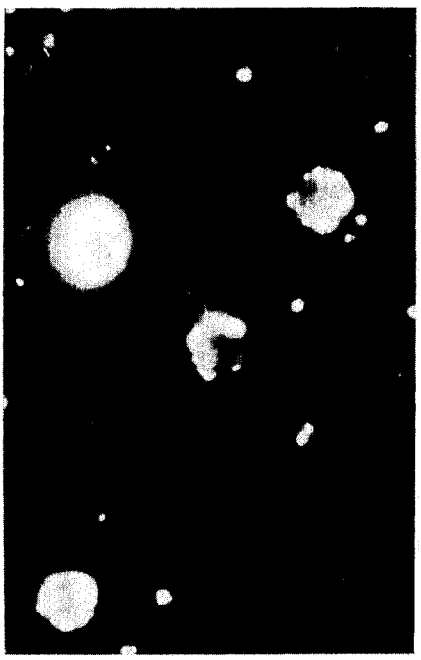
Figure 4G:
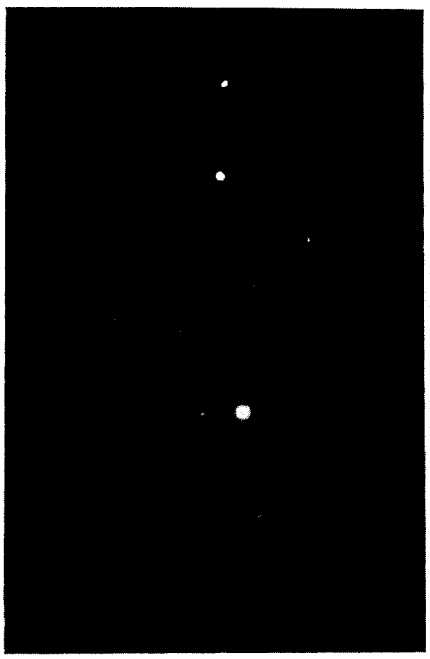

SA-liposomes with entrapped FITC-D were targeted to PC12 cells. Pretreatment of PC12 cells with biocytin-NGF produced fluorescent labeling of the cell periphery by these liposomes (FIG. 4A), whereas unmodified NGF did not (FIG. 4C). Fluorescent liposomes were also targeted to human melanoma cells of the HS294 line, which have $5-7 \times 10^5$ NGF receptors per cell (R. N. Fabricant, J. E. DeLarco and G. J. Todaro, "Nerve Growth Factor Receptors on Human Melanoma Cells in Culture", *Proc. Natl. Acad. Sci. USA.*, 74, 565-569, (1977)), a level 10- to 12-fold higher than that of PC12 cells (R. D. Vale and E. M. Shooter, "Assaying Binding of Nerve Growth Factor to Cell Surface Receptors",

*Methods in Enzymol.*, 109, 21-39, (1985)). Since for HS294 cells, the same level of fluorescence was observed immediately after the liposome incubation regardless of the temperature at which the cells were incubated with biocytin-NGF, the NGF-cell incubation was performed at 4° C. for all HS294 experiments described here. The observed level of targeted fluorescence on HS294 cells was much greater than that observed for PC12 cells when the cells were viewed in suspension immediately following liposome binding (FIG. 4E), whereas nonspecific binding was comparable to that observed for PC12 cells (FIG. 4G).

Figure 7B:
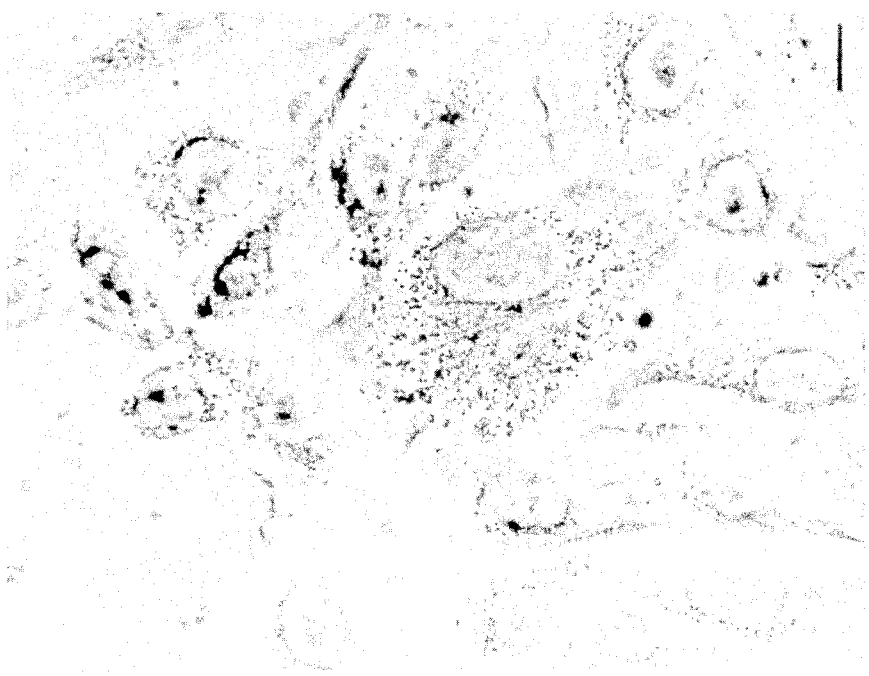
FIG. 7A and FIG. 7B are photographs of cells with targeted fluorescence
Figure 7A:
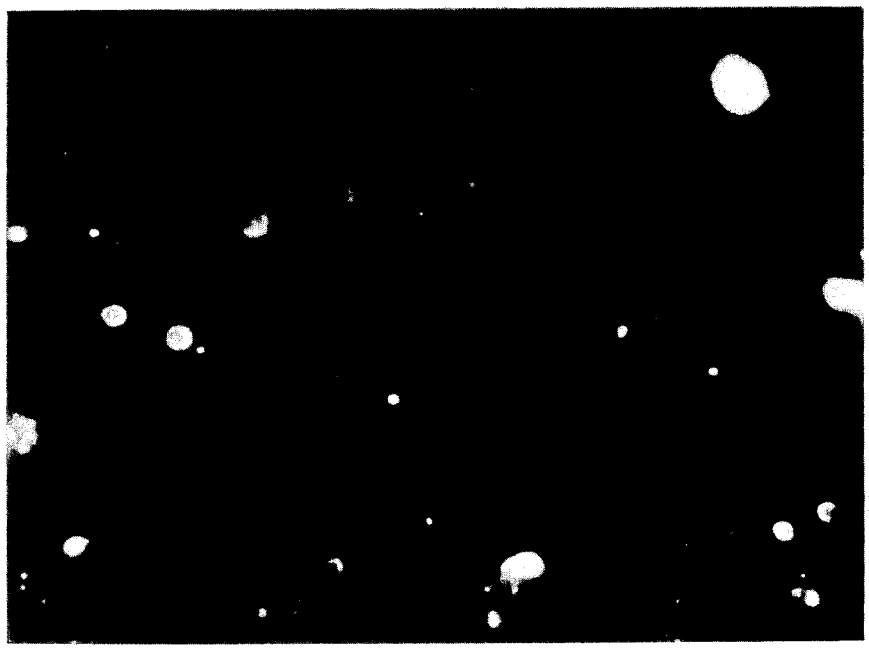
Figure 7D:
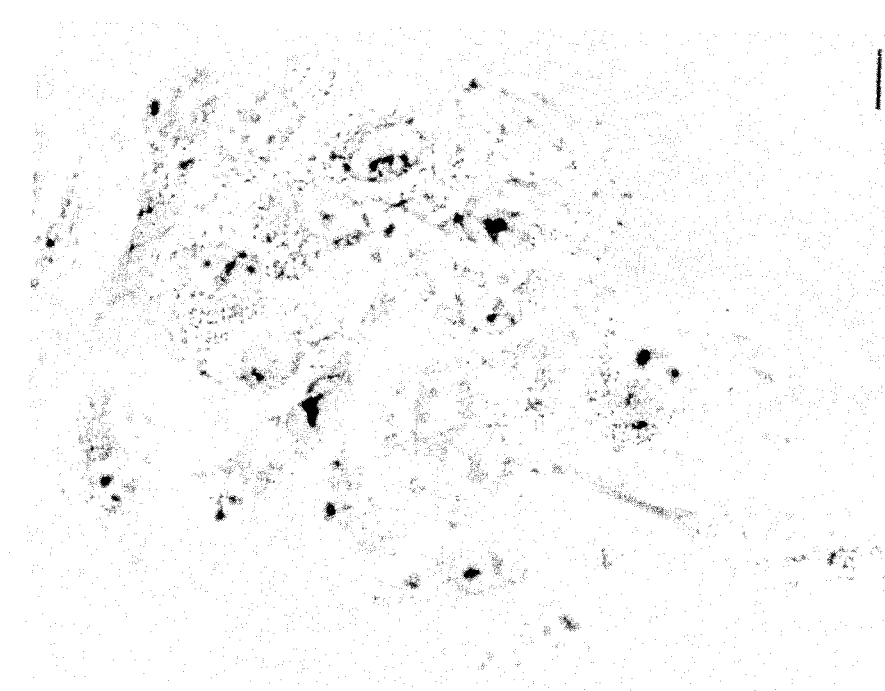
FIG. 7C and FIG. 7D are photographs of cells with control fluorescence
Figure 7C:
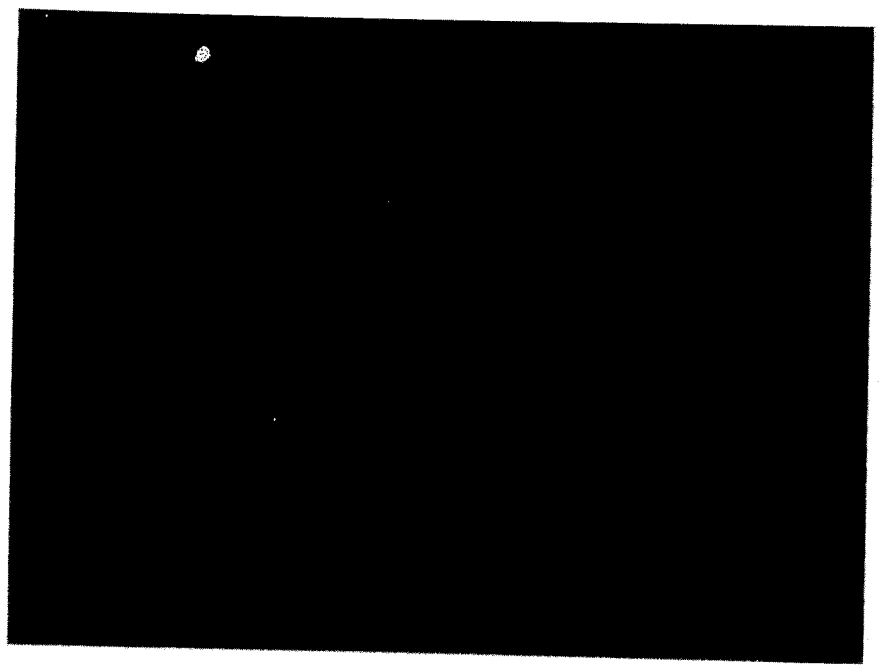

FIG. 5 depicts FITC-D distribution in attached cells. Cells with targeted liposome binding were treated as described above with regard to FIG. 4, were resuspended in D10 and plated onto four-well Lab Tek chamber slides. After incubation for 3 hours or overnight at 37° C., the cells were photographed in culture medium without fixation. FIG. 7A and FIG. 7B: HS294 cells incubated overnight; arrows indicate ruffled cellular protrusions which are not fluorescently labeled. FIG. 7C and FIG. 7D: PC12 cells incubated 3 hours.

Figure 5B:
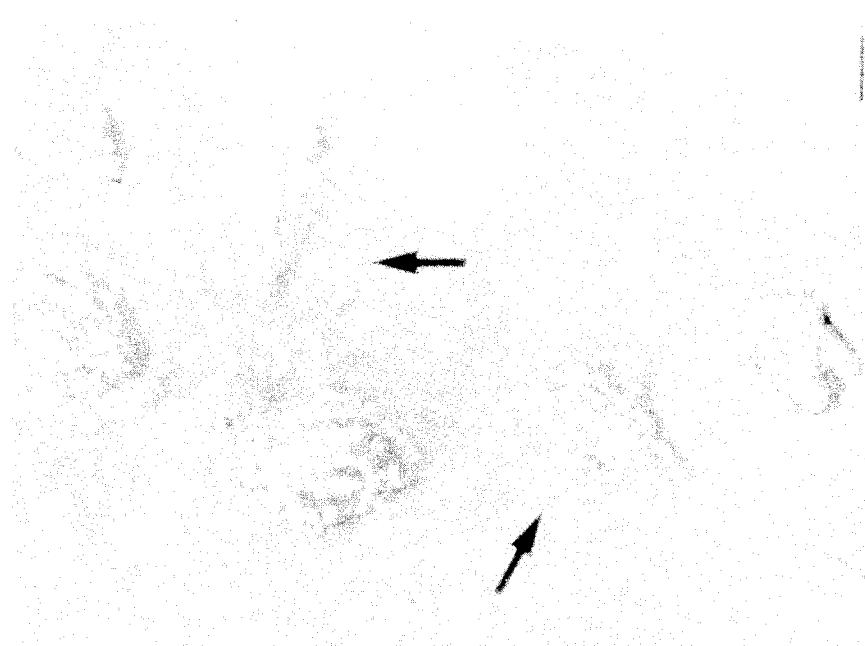
FIG. 5B is a photograph of a phase-contrast field for incubated HS294 cells.
Figure 5A:
FIG. 5A is a photograph of a fluorescence micrograph depicting incubated HS294 cells.
Figure 5E:
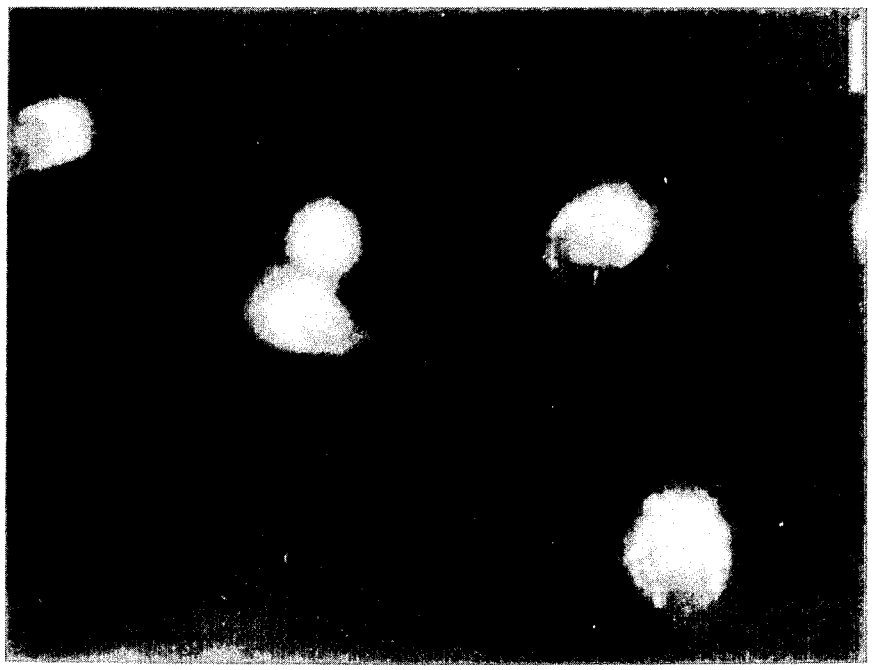
FIG. 5E is a photograph depicting HS294 cells stained with acridine orange to show the location of lyposomes. Bar equals 20 μm.
Figure 5C:
FIG. 5C is a photograph of a fluorescence micrograph for incubated PC12 cells.
Figure 5D:
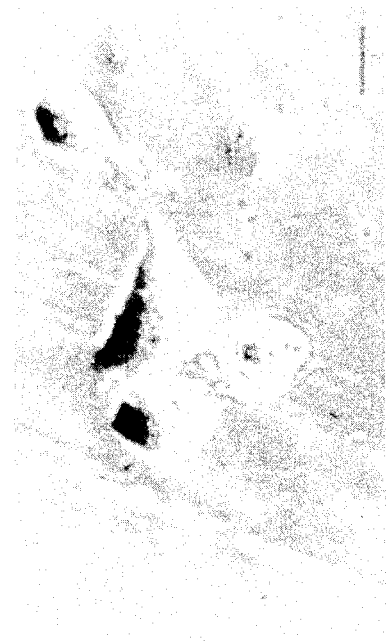
FIG. 5D is a photograph of a phase-contrast field for incubated PC12 cells.

When the fluorescently labeled HS294 cells were plated in growth medium and incubated at 37° C. for 3 hours (not shown) or overnight (FIG. 5A), the distribution of cell-associated fluorescence changed. Instead of uniform fluorescence around the cell periphery, a punctate pattern of fluorescence was observed, in 25-50% of the cells, that was associated with cell bodies proper and generally excluded from the thin cellular protrusions or filopodia that extended from the thin cellular protrusions of filopodia that extended across the surface of the substratum. In many cells, the fluorescence appeared to be perinuclear. When the cells were stained with acridine orange to identify lysosomes (A. C. Allison and M. R. Young, "Vital Staining and Fluorescence Microscopy of Lysosomes", *Lysosomes in Biology and Pathology*, Vol. 2, (J. T. Dingle and H. B. Fell, eds), pp. 600-628, Wiley Amsterdam, (1969)), the fluorescence pattern was similar to that observed with FITC-D liposomes (FIG. 5E), indicating that the liposomes were, indeed, in perinuclear locations. Although most PC12 cells were no longer labeled after a 3 hours incubation at 37° C., some exhibited a punctate pattern of fluorescence similar to that observed for HS294 cells (FIG. 5C).

Figure 6B:
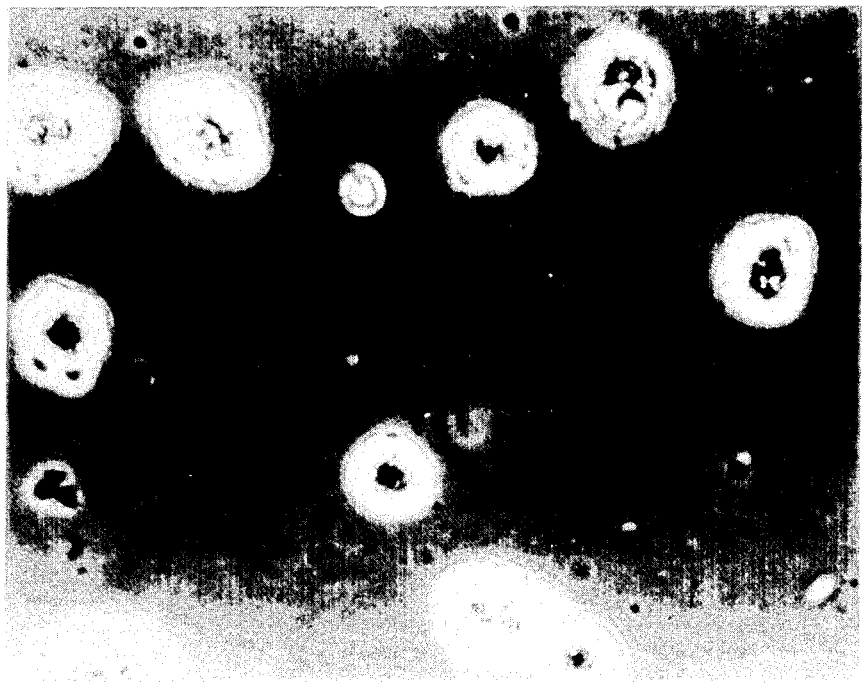
FIG. 6A and FIG. 6B are photographs of cells incubated at 4° C. prior to trypsin treatment.
Figure 6A:
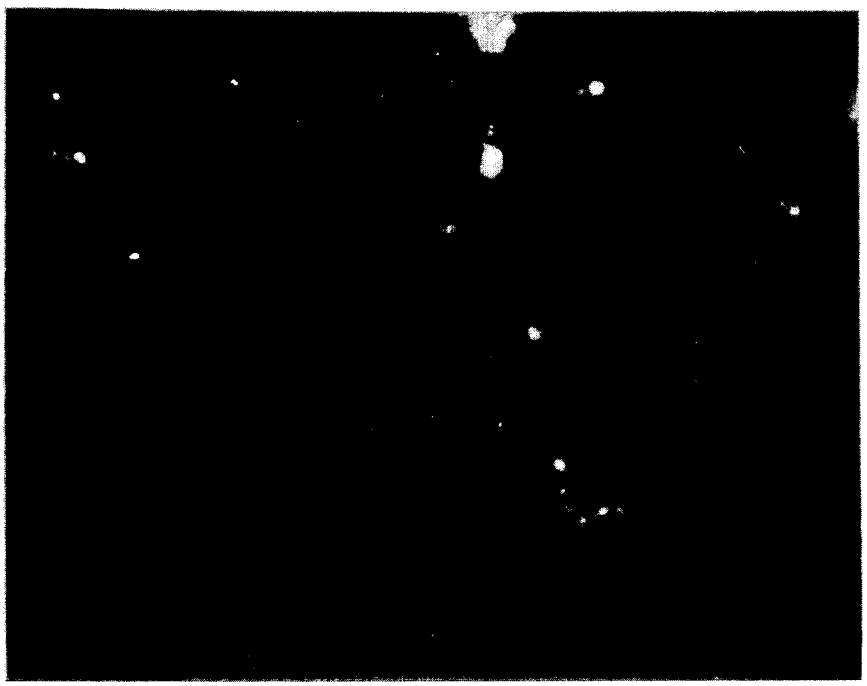
Figure 6D:
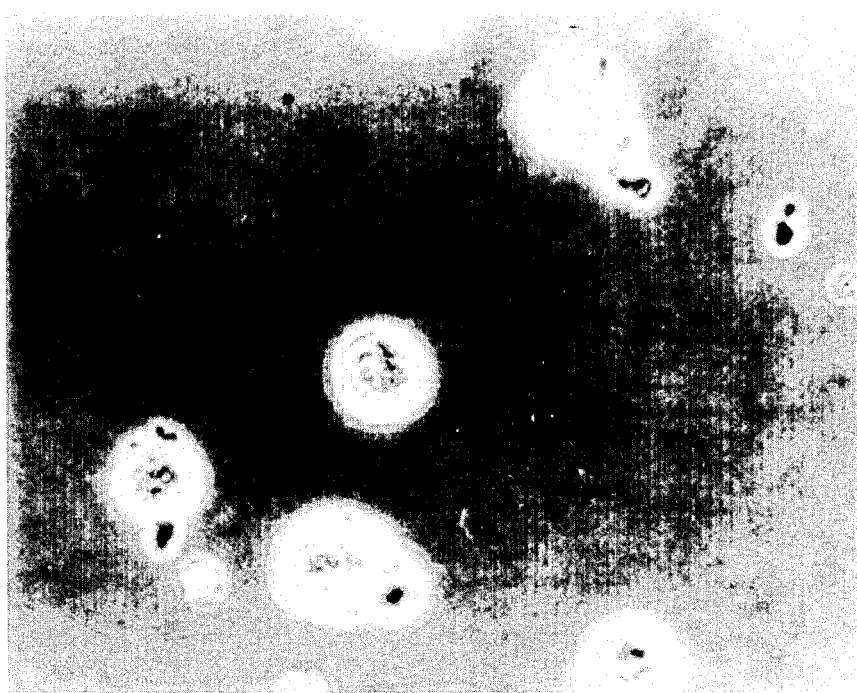
FIG. 6C and FIG. 6D are photographs of cells incubated overnight at 37° C. prior to treatment.
Figure 6C:
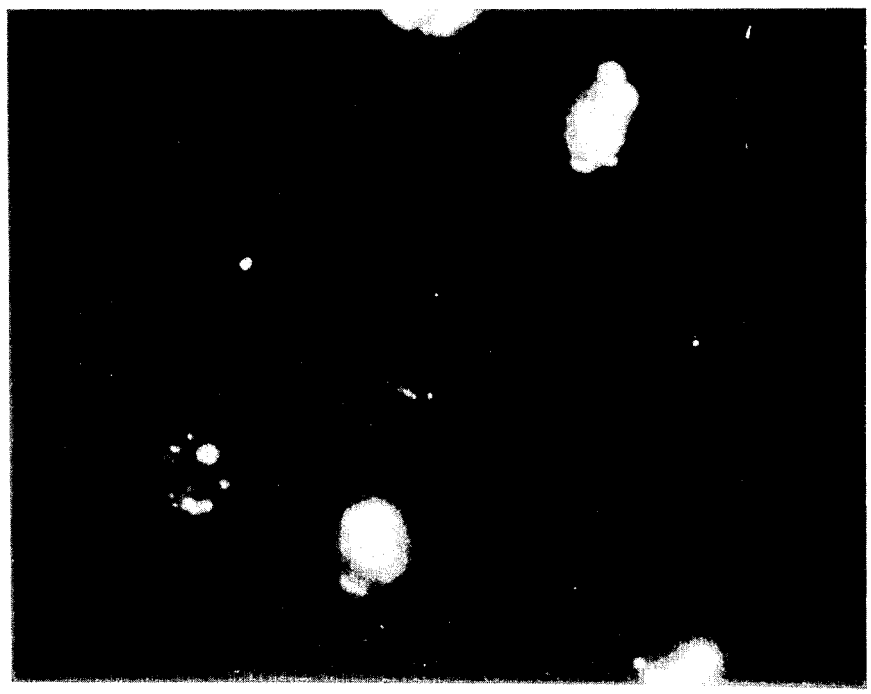

To determine whether the fluorescence associated with HS294 cells was internal rather than on the cell surface, as the microscopic investigations suggested, the cells with bound liposomes were incubated for 10 minutes at 4° C. with PBS containing 1 mg/ml trypsin and 1 mM EDTA. Cells that had been maintained at 4° C. following liposome binding were largely stripped of fluorescence by treatment with trypsin (FIG. 6A). In contrast, when cells were incubated overnight at 37° C. prior to trypsin treatment, most of the fluorescence was not removed (FIG. 6C), indicating that the liposomes were no longer present on the cell surface. Experiments using liposomes labeled with [$^3$H]DPPC indicated that approximately 10% of the liposomes initially bound remained associated with cells after overnight incubation at 37° C. and virtually all of this cell-associated label was resistant to trypsin treatment. The bulk of the liposomes presumably were not internalized, but instead dissociated from the cells during the overnight incubation. To demonstrate further internalization of liposome contents by HS294 cells, vesicles containing CF at a self-quenching concentration, 100 mM (Weinstein et al, 1984, supra), were targeted to cells. Cell-associated fluorescence was not observed immediately following liposome binding (not shown). Diffuse cytoplasmic fluorescence was visible, however, when the cells were maintained at 37° C. for 3 hours (not shown) or overnight (FIG. 7), suggesting that the CF had been delivered to an acidic compartment.

Discussion of Results

Biologically active derivatives of NGF, biotinylated via carboxyl groups were used to mediate the targeted binding of streptavidin-conjugated radiolabeled or fluorescently labeled liposomes to cells bearing NGF receptors, namely PC12 cells and HS294 human melanoma cells. The binding was specific, as it was greatly reduced when native NGF was used in place of the biotinylated derivatives or when hemoglobin was conjugated to liposomes in place of streptavidin (FIG. 2). Hemoglobin was used as a control because it is very similar to streptavidin in molecular weight, charge, and subunit composition. Nonconjugated liposomes exhibited background binding levels to cells similar to those observed for other controls (data not shown).

Incubation of PC12 cells with C-bio-NGF or biocytin-NGF at temperatures of 23 or 37° C. resulted in greater subsequent binding of SA-liposomes than did incubation at 4° C. (FIG. 3). P. Bernd and L. A. Greene, "Association of $^{125}$I-nerve Growth Factor with PC12 Pheochromocytoma Cells. Evidence for Internalization via High-affinity Receptors only and for Long-term Regulation by Nerve Growth Factor of both High- and Low-affinity Receptors", *J. Biol. Chem.*, 259, 15509-15516, (1984) previously observed a nearly sixfold increase in the amount of $^{125}$I-NGF bound to the surface of PC12 cells (i.e., acid-dissociable) when the temperature during a 30 minute incubation was increased from 4 to 37° C. Because the binding of $^{125}$I-NGF to PC12 cells is near maximum levels after 30 minutes at 4° C. (unpublished observation), their observation is not merely due to more rapid binding at 37° C. The apparent increase in NGF binding sites at elevated temperatures may be due to: (1) receptor rearrangement or an increase in membrane fluidity, allowing greater access of NGF to receptors; (2) an internal pool of receptors transported to the cell surface, (A. Cattaneo, S. Biocca, S. Nasi and P. Calissano, "Hidden Receptors for Nerve Growth Factor in PC12 Cells", *Eur. J. Biochem.*, 135, 285-290, (1983)), or (3) conversion of low-affinity NGF receptors to the high-affinity state, reducing the dissociation rate of biotinylated NGF from receptors during the liposome-cell incubation. The latter interpretation is difficult to evaluate because opinion is divided on whether receptor conversion actually occurs at 4° C. Some groups have reported that conversion is very low, (S. E. Buxser, D. J. Kelleher, L. Watson, P. Puma and G. L. Johnson, "Change in State of Nerve Growth Factor Receptor. Modulation of Receptor Affinity by Wheat Germ Agglutinin", *J. Biol. Chem.*, 258, 3741-3749, (1983)), or absent, (K. Herrup and H. Thoenen, "Properties of the Nerve Growth Factor Receptor of a Clonal Line of Rat Pheochromocytoma (PC12) Cells", *Exp. Cell. Res.*, 121, 71-78, (1979)), at 4° C., whereas others have reported that it is equal at 4 and 37° C., (R. D. Vale and E. M. Shooter, "Alteration of Binding Properties and Cytoskeletal Attachment of Nerve Growth Factor Receptors in PC12 Cells by Wheat Germ Agglutinin", *J. Cell Biol.*, 94, 710-717, (1982); R. D. Vale and E. M. Shooter, "Conversion of Nerve Growth Factor-Receptor Complexes to a Slowly Dissociating, Triton X-100 Insoluble State by Anti Nerve Growth Factor Antibodies", *Biochemistry*, 22, 5022–5028, (1983); P. M. Grob and M. A. Bothwell, "Modification of Nerve Growth Factor Receptor Properties by Wheat Germ Agglutinin", *J. Biol. Chem.*, 258, 14136–14143, (1983)).

The temperature effect was not observed with HS294 cells, which have a higher cell surface density of NGF receptors, primarily of low-affinity class (Vale and Shooter, 1985, supra).

If NGF-directed liposomes are to be used for the functional delivery of macromolecules, liposomal contents must be taken up by the target cells. This is of particular concern with melanomas, because apparently only high-affinity NGF receptors mediate endocytosis (P. Bernd and L. A. Greene, "Association of $^{125}$I-nerve Growth Factor with PC12 Pheochromocytoma Cells. Evidence for Internalization via High-affinity Receptors only and for Long-term Regulation by Nerve Growth Factor of both High- and Low-affinity Receptors", *J. Biol. Chem.*, 259, 15509–15516, (1984)), and cultured human melanoma cells are reported to have very low levels of this receptor class (Vale and Shooter, 1983, supra). In addition, small liposomes tend to be internalized more readily than large liposomes by some cell types, such as lymphomas, (P. Machy and L. D. Leserman, "Small Liposomes are Better than Large Liposomes for Specific Drug Delivery In Vitro", *Biochem. Biophys. Acta*, 730, 313–320, (1983); K. J. Matthay, T. D. Heath and D. Papahadjopoulos, "Specific Enhancement of Drug Delivery to AKR Lymphoma by Antibody Targeted Small Unilamellar Liposomes", *Cancer Res.*, 44, 1880–1886, (1984)). It might be anticipated, therefore, that melanomas would internalize the large liposomes used in this study very inefficiently, if at all. Several groups have demonstrated, however, that receptor clustering on PC12 and melanoma cells, mediated by wheat germ agglutinin or antibodies, may result in the conversion of low-affinity to high-affinity receptors (Vale an Shooter, 1982, supra, 1983, supra,; Buxser et al, 1983, supra; Grob and Bothwell, 1983, supra). By binding to biotinylated NGF molecules on several receptors simultaneously, SA-liposomes may also serve to aggregate receptors and thus cause a conversion to the apparent high-affinity state, thereby increasing the likelihood of endocytosis.

Three lines of evidence indicate that some liposomal contents were indeed internalized by HS294 cells. First, when liposomes containing FITC-D were bound to cells, most cell-associated fluorescence was removed by trypsin treatment from cells held at 4° C., a temperature at which endocytosis does not occur, (R. M. Steinman, I. S. Mellman, W. A. Muller and Z. A. Cohen, "Endocytosis and the Recycling of the Plasma Membrane", *J. Cell. Biol.*, 96, 1–27, (1983)). FIG. 6. depicts trypsin removal of surface-bound fluorescence. HS294 cells labeled with liposomes containing FITC-D were incubated with PBS containing 1 mg/ml trypsin and 1 mM EDTA for 10 minutes at 4° C. After the trypsin/EDTA was washed away, the cells were resuspended in HB-DMEM and photographed on glass slides under the glass coverslips. In contrast, most of the cell-associated fluorescence was inaccessible to trypsin treatment when cells were incubated overnight at 37° C. (FIG. 6).

Second, in cells incubated 3 hours or overnight at 37° C., FITC-D fluorescence was not observed in thin cellular extrusions, but was limited to the central cell body (FIG. 5). If the liposomes remained simply associated with the plasma membrane, the fluorescence would be expected to have been distributed randomly over the entire cell surface. In addition, a perinuclear fluorescence pattern similar to that observed when lysosomes were stained with acridine orange was clearly evident in some cells (FIG. 5).

Third, when liposomes containing CF at a self-quenching concentration were targeted to cells, no fluorescence was observed in cells held at 4° C. FIG. 7 depicts the uptake of CF by HS294 cells. HS294 cells were incubated with 1 μg/ml NGF (control) or biocytin-NGF (targeted), washed, and incubated with SA-liposomes containing 100 mM CF. Cells were separated from unbound liposomes by centrifugation through Ficoll, resuspended in D10, and plated onto four-well glass Lab Tek chamber slides. After an overnight incubation at 37° C., the cells were washed with PBS containing $Ca^{2+}$ and $Mg^{2+}$, fixed 10 minutes with 4% formaldehyde in PBS, mounted under glass coverslips with Glycergel (Accurate Chemicals), and photographed. Diffuse cytoplasmic fluorescence was present in cells incubated overnight at 37° C. (FIG. 7). The latter observation indicates further that some liposomal contents must have encountered acidic compartments as CF is a weak acid that has no net charge at low pH, allowing it to diffuse through membranes below pH 5.5 and be released into the cytoplasm, (R. M. Straubinger, K. Hong, D. S. Friend and D. Papahadjopoulos, "Endocytosis of Liposomes and Intracellular Fate of Encapsulated Molecules: Encounter with a Low pH Compartment after Internalization in Coated Vesicles", *Cell*, 32, 1069–1079, (1983)). Such low pH environments occur in endosomes or lysosomes, (M. C. Willingham and I. Pastan, "Endocytosis and Membrane Traffic in Cultured Cells", *Recent Prog. Hormone Res.*, 40, 569–587; Steinman et al, supra.). In contrast to CF, FITC-D cannot escape the lysosomal pathway (Straubinger et al, 1983, supra). Consistent with this, FITC-D targeted to cells continued to exhibit a punctate fluorescence pattern even after overnight incubation at 37° C. It is not clear why CF fluorescence was not detected in the nuclei of HS294 cells. Following liposomal delivery, internalized CF was observed in both the nuclei and cytoplasm and cultured monkey kidney cells (Straubinger et al, 1983, supra), but only in the cytoplasm of cultured mouse macrophages (Ivanov et al, 1985, supra).

Previous demonstrations of cell-specific liposome delivery have relied mainly on immunologic targeting methods (e.g., Leserman et al, 1980, supra; T. D. Heath, R. T. Fraley and D. Papahadjopoulos, "Antibody Targeting of Liposomes: Cell Specificity Obtained by Conjugation of F(ab')$_2$ to Vesicle Surface", *Science*, 210, 539–541, (1980)). The use of ligand-receptor interactions for liposome targeting, as described here, has not been widely pursued, having been reported only for low-density lipoproteins (Ivanov et al, 1985, supra) and insulin (Gitman et al, 1985, supra) and provides a new general strategy for liposome targeting. Such systems should complement immunological targeting and should serve to expand the usefulness of these systems by increasing the number of cell-specific targets and probes available. Using ligand-receptor interactions for liposome targeting also offers several possible advantages over immunological targeting. Many ligands bind to receptors more avidly than antibodies bind to antigens. Antibody-antigen interactions have dissociation constants ($K_D$ values) in the range of $10^{-6}$–$10^{-9}$, with the higher affinity interactions bring relatively uncommon, (J. W. Goding, Monoclonal Antibodies: Principles and Practice, p. 44, Academic Press, Orlando, (1983)), whereas many hormone-receptor interactions have dissociation constant ($K_D$) values ranging from $10^{-9}$ to $10^{-11}$, (C. R. Kahn, "Membrane Receptors for Hormones and Neurotransmitters", *J. Cell Biol.*, 70, 261–286, (1976). In addition, it may be possible to use ligand-receptor interactions to deliver liposomal contents into the cell more efficiently than is possible with immunological targeting. P. Machy, J. Barbet and L. D. Leserman, "Differential Endocytosis of T and B Cell Surface Molecules Evaluated with Antibody-bearing Fluorescent Liposomes Containing Methotrexate", *Proc. Natl. Acad. Sci. U. S. A.*, 79, 4148–4152, (1982), targeted fluorescent methotrexate-containing liposomes to various surface antigens on mitogen-stimulated T and B spleen cells. Internalization of the liposomes, as assessed by methotrexate inhibition of [$^3$H]dUdR incorporation, was not a function of the number of liposomes bound, as assessed by fluorometry, but rather was a function of both the cell type and target molecules, indicating that individual cell surface determinants were internalized at different rates. Thus, various surface antigens appear to be internalized constitutively, others are internalized rapidly only when occupied by ligands, whereas others are not rapidly internalized even when complexed with ligands (Willingham and Pastan, 1984, supra). By carefully selecting the appropriate ligand-receptor interaction for liposome targeting, therefore, one may be able to enhance the uptake of liposomes by target cells.

The present data indicate that the NGF-directed targeting system can deliver biological materials to the cellular lysosomal pathway and that weakly acidic molecules such as CF, which are charged at neutral pH but uncharged at acidic pH, can escape this pathway and enter the cytoplasm. In many targeting applications, however, it will be desirable to deliver materials into the cytoplasm that, like cytosine-$\beta$-D-arabinofuranoside, cannot normally escape a lysosomal fate. For these applications, it may be possible to use pH-sensitive liposomes. R. M. Straubinger, N. Duzgunes and D. Papahadjopoulos, "pH-sensitive Liposomes Mediate Cytoplasmic Delivery of Encapsulated Macromolecules", *FEBS Lett.*, 179, 148–154, (1985), determined that liposomes composed of a 7:3 ratio of phosphatidylethanolamine and oleic acid become unstable below pH 7. They used these liposomes to introduce calcein, a compound similar to CF, but more acidic, into cultured monkey kidney cells. When calcein is introduced into these cells with normal pH-stable liposomes, unlike CF it does not become neutral and thereby lipid permeable to acidic pH. Consequently, it is retained in endosomes and lysosomes (Straubinger et al, 1983, supra). When calcein was introduced into these cells using the pH-sensitive liposomes, however, diffuse cytoplasmic fluorescence was observed, indicating fusion of the unstable liposomes with endocytic vesicles during acidification (Straubinger et al, 1985, supra). J. Connor and L. Huang, "Efficient Cytoplasmic Delivery of a Fluorescent Dye by pH-sensitive Liposomes", *J. Cell Biol.*, 101, 582–589, (1985), also used pH-sensitive liposomes, composed of an 8:2 ratio of dioleoylphosphatidylethanolamine and palmitoyl-homocysteine, for the antibody-targeted delivery of calcein into the cytoplasm of mouse cells bearing H2-K$^k$ antigens. An alternative approach for introducing molecules into the cytoplasm would be to incorporate fusion proteins from enveloped viruses into the liposomal membrane. These proteins allow the viruses, which enter the cells by adsorptive pinocytosis, to escape the lysosomal pathway by inducing fusion between the viral and endosomal membranes at a pH of 5–6, (M. Marsh, "The Entry Enveloped Viruses into Cells by Endocytosis", *Biochem. J.*, 218, 1–10, (1984)).

The targeting system of the present invention has the potential for the selective therapeutic delivery of anticancer drugs to melanomas, pheochromocytomas and neuroblastomas without affecting other cells types, such as hematopoietic cells. Indeed, in preliminary experiments, HS294 cells have been killed in vitro through the targeted delivery of methotrexate. The use of NGF-directed liposomes for targeted gene transfer could be extremely useful for future gene therapy applications.

It will be appreciated that the instant specification and claims are set forth by way of illustration and not limitation, and that various modifications and changes may be made without departing from the spirit and scope of the present invention.

What is claimed is:

1. A liposome conjugated with a protein which binds biotin, said liposome comprising phospholipid amino groups, said protein which binds biotin further comprises carboxyl residues, said carboxyl residues being coupled to phospholipid amino groups of the liposome via a coupling reagent, wherein the protein which binds biotin is streptavidin and wherein the ratio of the concentration of the coupling reagent to the phospholipid concentration is up to 100 mg/ml of coupling reagent per 5μmol/ml of phospholipid and whereby said liposome is not cross-linked to other liposomes.

2. A liposome according to claim 1, wherein the phospholipid amino groups are on phosphatidylethanolamine molecules residing in pre-formed liposomes.

3. A liposome according to claim 1, wherein the liposomes are unilammelar liposomes.

4. A method for preparing a liposome conjugated with a protein which binds biotin, the method comprising carbodiimide-mediated coupling of carboxyl residues on said protein which binds biotin to amino groups residing on phosphatidylethanolamine molecules residing in preformed liposomes, wherein said protein which binds biotin is streptavidin and wherein the ratio of the concentration of carbodiimide to the concentration of phospholipid is up to 100 mg/ml carbodiimide per 5μmol/ml of phospholipid and whereby said liposome is not cross-linked to other liposomes.

5. A method for the site-directed delivery of drugs or cytotoxic agents into the cells of a host comprising
  (a) encapsulating said drug or cytotoxic agent within a liposome according to claim 1,
  (b) attaching biotin or a biotin-containing compound to a ligand or antibody for said site,
  (c) injecting the product of step (b) into the host and
  (d) injecting the product of step (a) into the host.

6. A method according to claim 5, wherein the product of step (a) is combined with the product of step (b) and the resultant combined product is injected into the host.

7. A method for the site-directed delivery of drugs or cytotoxic agents in a host comprising
  (a) encapsulating said drug or cytotoxic agent within a liposome according to claim 1 and injecting said encapsulated liposome to a tissue sample ex corpora, (b) attaching biotin or a biotin-containing compound to a ligand or antibody for said site,
(c) injecting the product of step (b) into the host and
(d) injecting the product of step (a) into the host.

8. A method according to claim 5, wherein the product of step (a) is combined with the product of step (b) and the resultant combined product is injected into the host.

9. A liposome according to claim 1, wherein the protein which binds biotin is C-bio-NGF.

10. A liposome according to claim 1, wherein the protein which binds biotin is biocytin-NGF.

11. A method according to claim 4, wherein the protein which binds biotin is C-bio-NGF.

12. A method according to claim 4, wherein the protein which binds biotin is biocytin-NGF.

* * * * *